US007136703B1

(12) United States Patent
Cappa et al.

(10) Patent No.: US 7,136,703 B1
(45) Date of Patent: Nov. 14, 2006

(54) PROGRAMMER AND SURFACE ECG SYSTEM WITH WIRELESS COMMUNICATION

(75) Inventors: Armando M. Cappa, Granada Hills, CA (US); Sergiu Silvian, La Crescenta, CA (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 485 days.

(21) Appl. No.: 10/123,944

(22) Filed: Apr. 16, 2002

(51) Int. Cl.
*A61N 1/362* (2006.01)

(52) U.S. Cl. ............................................ 607/9; 607/30
(58) Field of Classification Search .................... 607/9, 607/30, 32; 600/508–509, 522; 128/903
See application file for complete search history.

(56) References Cited

U.S. PATENT DOCUMENTS

| 4,981,141 | A |   | 1/1991  | Segalowitz ................. 128/696 |
|-----------|---|---|---------|-------------------------------------|
| 5,168,874 | A |   | 12/1992 | Segalowitz ................. 128/639 |
| 5,307,818 | A | * | 5/1994  | Segalowitz ................. 600/509 |
| 5,383,915 | A |   | 1/1995  | Adams ........................ 607/60 |
| 5,507,782 | A | * | 4/1996  | Kieval et al. .................. 607/9 |
| 5,511,553 | A |   | 4/1996  | Segalowitz ................. 128/696 |
| 5,605,158 | A | * | 2/1997  | Snell .......................... 600/508 |
| 5,720,770 | A |   | 2/1998  | Nappholz et al. ............. 607/30 |
| 5,724,025 | A |   | 3/1998  | Tavori ........................ 340/573 |
| 5,749,907 | A | * | 5/1998  | Mann .......................... 607/27 |
| 5,833,623 | A | * | 11/1998 | Mann et al. ................. 600/523 |
| 5,871,451 | A | * | 2/1999  | Unger et al. ................. 600/509 |
| 6,038,469 | A |   | 3/2000  | Karlsson et al. ............ 600/512 |
| 6,073,046 | A |   | 6/2000  | Patel et al. .................. 600/509 |
| 6,149,602 | A |   | 11/2000 | Arcelus ....................... 600/523 |
| 6,161,039 | A |   | 12/2000 | Krichen et al. ............. 600/523 |
| 2002/0143372 | A1 | * | 10/2002 | Snell et al. ................... 607/30 |

FOREIGN PATENT DOCUMENTS

WO    WO 01/78831 A2    4/2001

\* cited by examiner

*Primary Examiner*—Carl Layno

(57) ABSTRACT

A programmer for implantable stimulation devices and surface ECG system in wireless communication with each other. A self-powered ECG monitor with conventional surface electrodes transceives signals from and to a programmer provided with a radio frequency transceiver to eliminate hardwiring between the surface electrodes and the programmer. The system reduces the need for supply line frequency filtering and isolation circuitry to protect against high voltage defibrillation shocks.

8 Claims, 6 Drawing Sheets

| EXT. CONTROL | | | LEAD | SWITCH CONTROL 136 | | | | | | | −INPUT | +INPUT |
|---|---|---|---|---|---|---|---|---|---|---|---|---|
| DEC. | $I_2$ $I_1$ $I_0$ | | | A | B | C | D | E | F | G | | |
| 7 | 1 1 1 | | — | X | | | | | | | — | — |
| 6 | 1 1 0 | | V | | | | | X | X | X | $\frac{RA+LA+LL}{3}$ | C |
| 5 | 1 0 1 | | aVF | | | | X | X | X | | $\frac{RA+LA}{2}$ | LL |
| 4 | 1 0 0 | | aVL | | | X | | X | X | X | $\frac{RA+LL}{2}$ | LA |
| 3 | 0 1 1 | | aVR | | | | X | X | X | X | $\frac{LA+LL}{2}$ | RA |
| 2 | 0 1 0 | | III | | | | X | X | | | LA | LL |
| 1 | 0 0 1 | | II | | | | | | X | | RA | LL |
| 0 | 0 0 0 | | I | | X | | | | X | | RA | LA |

X = SWITCH ON (CLOSED)

FIG. 6

PROGRAMMER AND SURFACE ECG SYSTEM WITH WIRELESS COMMUNICATION

FIELD OF THE INVENTION

The present invention relates to the field of cardiac monitoring devices and, in particular, to a combined programmer for implantable cardiac devices and a surface ECG system with a wireless communication capability with the programmer.

BACKGROUND OF THE INVENTION

The ongoing clinical care provided to patients with implantable cardiac device systems often includes the use of surface electrocardiograms (ECG). An ECG is a highly useful diagnostic aid for clinicians for the study of heart rate and rhythm. The ECG indicates the propagation of low amplitude electrical signals, commonly referred to as the cardiac impulse, across the myocardium giving information about depolarization and repolarization characteristics of the heart.

An ECG typically receives signals from a plurality of electrodes (3, 5, and 12 are common numbers) that are placed on the patient's skin surface. The ECG monitors voltage signals appearing between various pairs of the electrodes and performs a vector analysis of the resultant signal pairs to prepare various two-dimensional voltage-time graphs indicative of internal cardiac activity. Surface ECG refers to placement of electrodes on the surface, or skin, of the patient as opposed to directly to cardiac tissue which obviously requires an invasive procedure.

A programmer is a device that enables a clinician to telemetrically communicate with an implantable cardiac device such as pacemaker or defibrillator. Implantable devices often monitor and record a variety of internal physiological parameters of the patient and are often provided with a telemetry system to telemetrically transmit those measured and recorded parameters outside the patient's body. Implantable devices are also often capable of receiving telemetric signals to induce the device to set or change a variety of operational parameters of the device as well as to select among the physiological parameters that the device monitors and records. These parameters are often desirably changed during the implantation period to adjust the therapy provided and/or physiological parameters monitored in order to provide the attending clinician with different information or to adapt the therapy to a more efficacious regimen. It is highly desirable to set these parameters without the expense and health risks to the patient of an invasive procedure. The programmer enables the attending clinician to perform these tasks in a non-invasive, telegraphic manner.

A surface ECG is often used along with the programmer as the surface ECG provides additional information above that provided by the internal measurements obtained by the implantable device. The programmer is typically adapted to obtain a surface ECG through a special cable that generally interconnects the programmer to electrodes placed on the patient. As the programmer is thus electrically coupled to the patient, it is subject to exposure to electromagnetic interference (EMI) that may surround the interconnection. The programmer is also potentially subject to large common-mode 50/60 Hz (supply line frequency) signals that are picked up by the patient's body. Both EMI and common-mode signals degrade the accuracy of the ECG signal.

An additional concern in certain applications where defibrillation may be applied to the patient is the relatively large amplitude (hundred volt to kilovolt range) shocks that are typically applied to interrupt the fibrillation. These high voltage shocks can be conducted through other cabling interconnecting the patient and other equipment such as programmers. Accordingly, the front-end electronics (those directly in contact with the cabling) of the programmer generally require voltage protection adequate to prevent damage from up to 5000V that may be applied to the patient as defibrillation. The inclusion of such protection circuitry increases the cost and complexity of programmers.

The interconnection cable employed in prior art programmers with surface ECG systems presents some further difficulties in use for the clinician and for the patient. The cable is physically attached to the patient and impairs their movement in bed and can become entangled with bedding, I.V. tubes, etc. The cables also physically interconnect the programmer to the patient and thus present a physical obstacle that must be avoided by people moving in the room. The cables present a tripping hazard as well as a potential cause of upset and damage to the programmer or other devices that may be placed on tables or carts.

Another disadvantage of present programmer/ECG systems is that the clinician must physically connect the programmer to surface electrodes with the interconnection cable each time he visits a new patient. Often an individual programmer is not available for each patient due to cost considerations and the clinician must move a single programmer with him as he visits patients. It can be appreciated that disconnecting and reconnecting the cables each time a clinician visits a patient consumes the doctor's valuable time as well as presents a cause of wear and tear on the cables and connectors.

From the foregoing it can be appreciated that there is an ongoing need for a programmer/ECG system that reduces the need for obtrusive and hazardous cables. There is also a need for a system that facilitates movement of the clinician from patient to patient in different locations and maintains the functionality of programmers in communication with surface ECGs without the expense of providing a dedicated programmer at each patient location.

SUMMARY OF THE INVENTION

The aforementioned needs are satisfied by the invention which, in one aspect, is a system that communicates with and programs an implantable stimulation device and obtains a surface ECG signal, the system comprising a wireless ECG monitoring system including an electrode system adapted to adhere to a patient's skin in desired locations and provide a plurality of electrode signals, and an ECG monitor adapted to be worn by the patient and coupled to the electrode system so as to receive the plurality of electrode signals, the ECG monitor having circuitry to transmit a plurality of surface ECG signals and a programmer including a first telemetry circuit that transceives programming signals and data with the implantable stimulation device, a second telemetry circuit that receives the plurality of ECG signals from the wireless ECG monitoring system, and a display system that graphically displays the received surface ECG signals.

These aspects of the invention can also include the feature wherein the system includes a sensing system that senses each electrode signal and a signal processor that processes each electrode signal into at least one of a Lead I, Lead II, Lead III, $aV_R$ Lead, an $aV_L$ Lead, an $aV_F$, or a V Lead or wherein the wireless ECG monitoring system further includes a sensing system that senses each electrode signal and a signal processor that processes each electrode signal into at least one of a Lead I, Lead II, or Lead III. In the later aspect, the signal processor can further process each electrode signal into one of an $aV_R$ Lead, an $aV_L$ Lead, an $aV_F$, or a V Lead.

The invention also includes the aspect wherein the ECG monitoring system further includes a plurality of switches connected to the electrode signal to enable selection among the plurality of electrode signals. In this aspect, the plurality of switches can be electronic and selection among the plurality of electrode signals occurs in response to control signals from the programmer or the plurality of switches are manually operated to select among the plurality of electrode signals.

Another aspect of the invention is wherein the first and second telemetry links utilize a first and second channel respectively for independently processing the programming signals and the data signals with the implantable stimulation device from the plurality of surface ECG signals from the wireless ECG monitoring system. Under this aspect, the first and second channels can comprise first and second frequency channels, first and second time division channels, or first and second modulation channels. This aspect can further include wherein at least one of the first and second telemetry circuits operate in the 900 MHz band.

An additional aspect of the invention is a monitoring system for an implantable cardiac stimulation device, the monitoring system comprising a programmer that includes a telemetry receiver so as to be able to receive signals from an implantable cardiac stimulation device, wherein the programmer includes a display that displays information about the performance of the implantable device and a surface monitoring system that includes at least one electrode that is adapted to be positioned on the body of the patient so as to produce a surface signal indicative of the patient's heart function, wherein the surface monitoring system includes a wireless transmitter that transmits signals to the programmer indicative of the surface signal and wherein the programmer is further adapted to display the surface signal on the display to permit simultaneous evaluation of the information about the performance of the implanted device provided via the telemetry receiver and the surface signal.

A particular aspect therein is that the surface signal comprises an ECG and can further comprise at least one of a Lead I, Lead II, Lead III, $aV_R$ Lead, an $aV_L$ Lead, an $aV_F$, or a V Lead.

Yet another aspect is that the programmer, the implantable device, and the surface monitoring system each include a telemetry transceiver such that the programmer, the implantable device, and surface monitoring system can each both send and receive wireless signals. This aspect can include wherein communication between the programmer and the implantable device occurs on a first RF channel and communication between the programmer and the surface monitoring system occurs on a second RF channel and further that at least one of the first and second RF channels operate in the 900 MHz band.

Further aspects of the invention include that the system comprises a plurality of electrodes. Additionally, the surface monitoring system can select from among the plurality of electrodes to send signals to the programmer indicative of the selected signals. Further, signals from the programmer induce the surface monitoring system to select signals from among the plurality of electrodes to send signals to the programmer indicative of the selected signals or the system further comprises a plurality of switches connected to the plurality of electrodes wherein the switches are manually operated to select among the plurality of electrodes.

Alternatively, the surface monitoring system sends signals corresponding to all of the plurality of electrodes to the programmer and the programmer selects from among the signals corresponding to the plurality of electrodes to determine the surface signal to display.

The invention is also a therapeutic stimulation and monitoring system for a patient's heart comprising an implantable cardiac stimulation and physiological parameter monitoring device, a programmer adapted to transceive wireless signals with the implantable device so as to induce the implantable device to alter the therapeutic stimulation and monitored physiological parameters provided and to transmit signals indicative of the monitored physiological parameters to the programmer, and means for monitoring surface signals of the patient indicative of cardiac activity including means for transceiving wireless signals with the programmer so as to provide the programmer with signals indicative of the surface signals of the patient and to receive signals inducing the monitoring means to alter the configuration of the surface signal provided to the programmer.

Particular aspects thereunder include wherein the programming means further comprises display means for displaying signals indicative of the surface signals of the patient. The surface signals can comprise a surface electrocardiogram that can comprise at least one of a Lead I, Lead II, Lead III, $aV_R$ Lead, an $aV_L$ Lead, an $aV_F$, or a V Lead.

A further aspect of the invention is wherein the monitoring means provides the programmer with signals selected from among a plurality of the surface signals. Here the monitoring means can select among the plurality of surface signals in response to wireless signals from the programmer or the therapeutic stimulation and monitoring system can further comprise a plurality of switches that are manually actuated to select among the plurality of surface signals.

In addition, the implantable device and the programmer can communicate via first wireless communication means and the programmer and the monitoring means can communicate via second wireless communication means. This can occur such that at least one of the first and second wireless communications means operate in the 900 MHz band. These and other objects and advantages will be more apparent from the following description taken in conjunction with the accompanying drawings.

BRIEF DESCRIPTION OF THE DRAWINGS

FIG. 6 is a table of one embodiment of the control logic for achieving various lead configurations in the system of FIG. 1.

DETAILED DESCRIPTION OF THE PREFERRED EMBODIMENTS

Figure 1:
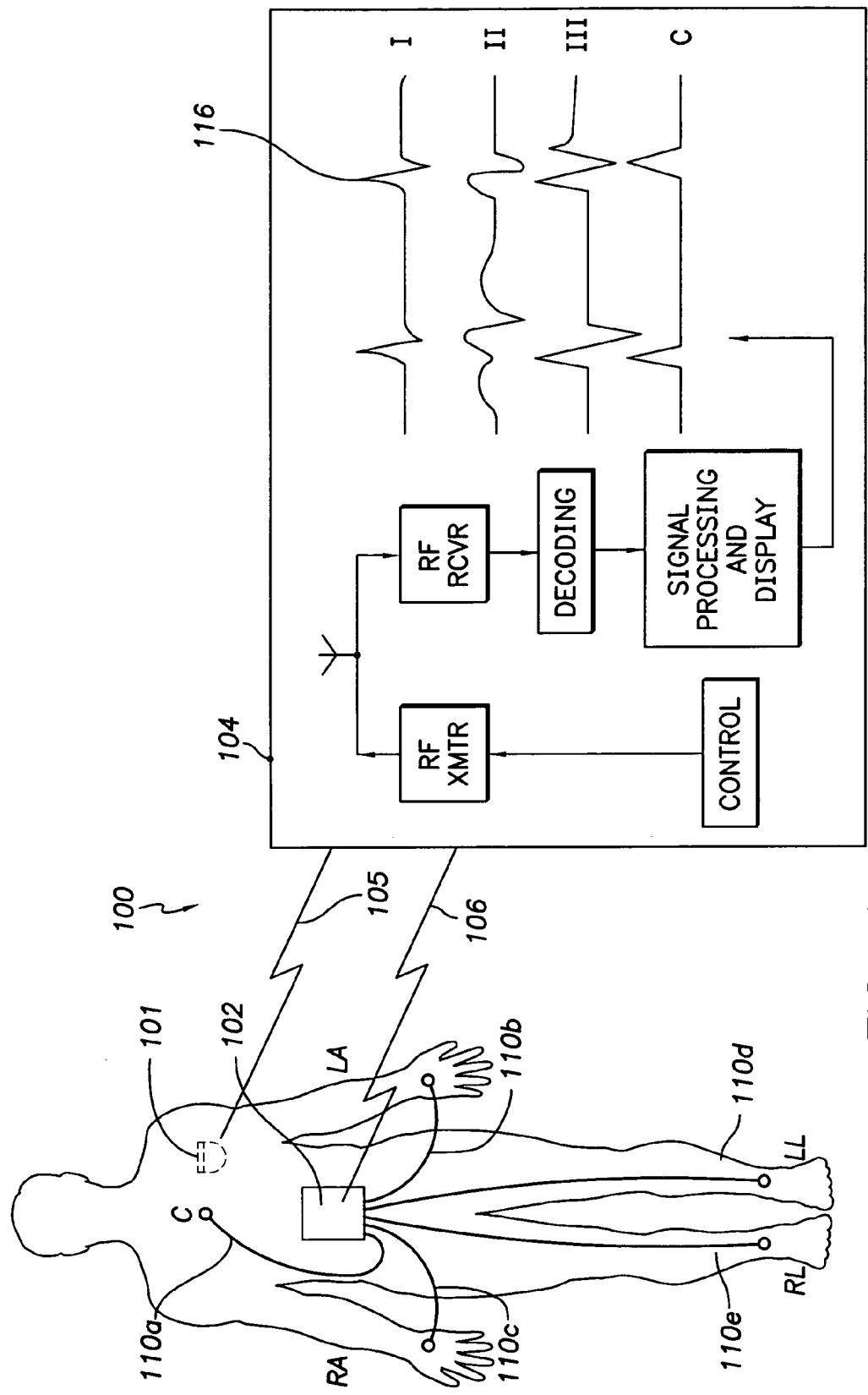
FIG. 1 is a high-level block diagram of an implantable stimulation device programmer and surface ECG system with wireless communication having a five electrode configuration.

Reference will now be made to the drawings wherein like numerals refer to like parts throughout. FIG. 1 illustrates a programmer for implantable cardiac devices and surface electrocardiogram (ECG) monitor with wireless communication system 100 referred to hereafter as "system 100" for brevity. The system 100 enables a clinician to program and retrieve information from an implantable stimulation device (not shown) via a first telemetric link 105 and to receive and control surface ECG signals in a wireless fashion from the patient via a second telemetric link 106 in a manner that will be described in greater detail below.

The system 100 comprises an ECG monitor 102 that monitors surface ECG signals of a patient's body and selectively transmits those signals to a remote programmer 104 via the second telemetric link 106. The second telemetric link 106 reduces the need for the hardwiring of the prior art between an ECG monitor and a programmer while enabling the surface ECG monitor 102 and the programmer 104 to remain in communication with each other.

The surface ECG monitor 102 comprises a plurality of electrodes 110, 111. In one embodiment (FIG. 1), the ECG monitor 102 comprises 5 electrodes 110a–110e and in another embodiment (FIG. 2) the ECG monitor 102 comprises 3 electrodes 111a–111c. However, other embodiments can comprise alternative numbers of electrodes 110, 111. The electrodes 110, 111 monitor electrical activity on the skin surface of a patient indicative of internal cardiac activity in a known manner. The electrodes 110, 111 are placed and secured to a patient's body in a manner well understood in the art.

Figure 2:
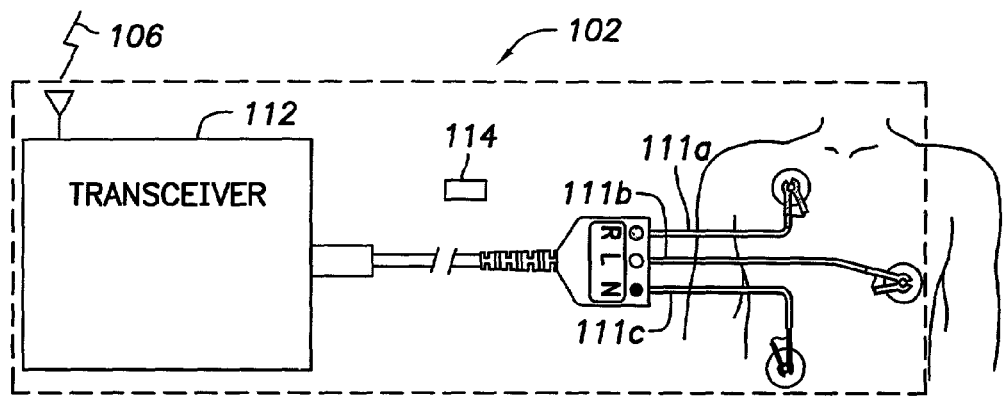
FIG. 2 illustrates a surface ECG unit with wireless communication capability and with three electrodes adhered to a patient.

In one embodiment, the electrodes 110 are unitized pieces including a sensor section placed on the patient's body and a fixedly attached conductive line. In another embodiment, the electrodes 111 are separable assemblies including a sensor section removably attached to a conductive line as illustrated in FIG. 2. The electrodes 110, 111 are commercially available.

As shown in FIG. 2, the ECG monitor 102 also comprises a transceiver 112 providing the second telemetric link 106 with the programmer 104. The transceiver 112 is a self-powered radio transceiver and, in this embodiment, operates in the 900 MHz band. However, other frequencies can be employed in alternative embodiments of the transceiver 112 without detracting from the scope of the invention. It will be understood by one of skill in the art that the frequencies utilized by the transceiver 112 should be chosen so as to minimize interference with other electronic devices in use in the vicinity of the system 100. The transceiver 112 selectively transmits signals monitored by the electrodes 110, 111 to the programmer 104. In one embodiment, the transceiver 112 also receives signals from the programmer 104 to vary the electrodes 110, 111 from whose measurements the transceiver 112 sends to the programmer 104.

In one embodiment, the ECG monitor 102 includes a switch (FIG. 2) 114. The switch 114 is interposed between the electrodes 111a–111c and the transceiver 112 so as to selectively connect or disconnect the individual electrodes 111a–111c from the transceiver 112 so as to enable selection of the electrodes 111a–111c whose signals are passed to the transceiver 112. This aspect facilitates ready selection of a number of different lead configurations by the clinician. In one embodiment, the switch 114 is a manually operated switch, however, in other embodiments, the selection of the electrodes 110, 111 is performed electronically in response to telegraphic signals from the programmer 104 in a manner that will be described in greater detail below with reference to FIG. 5.

Figure 3:
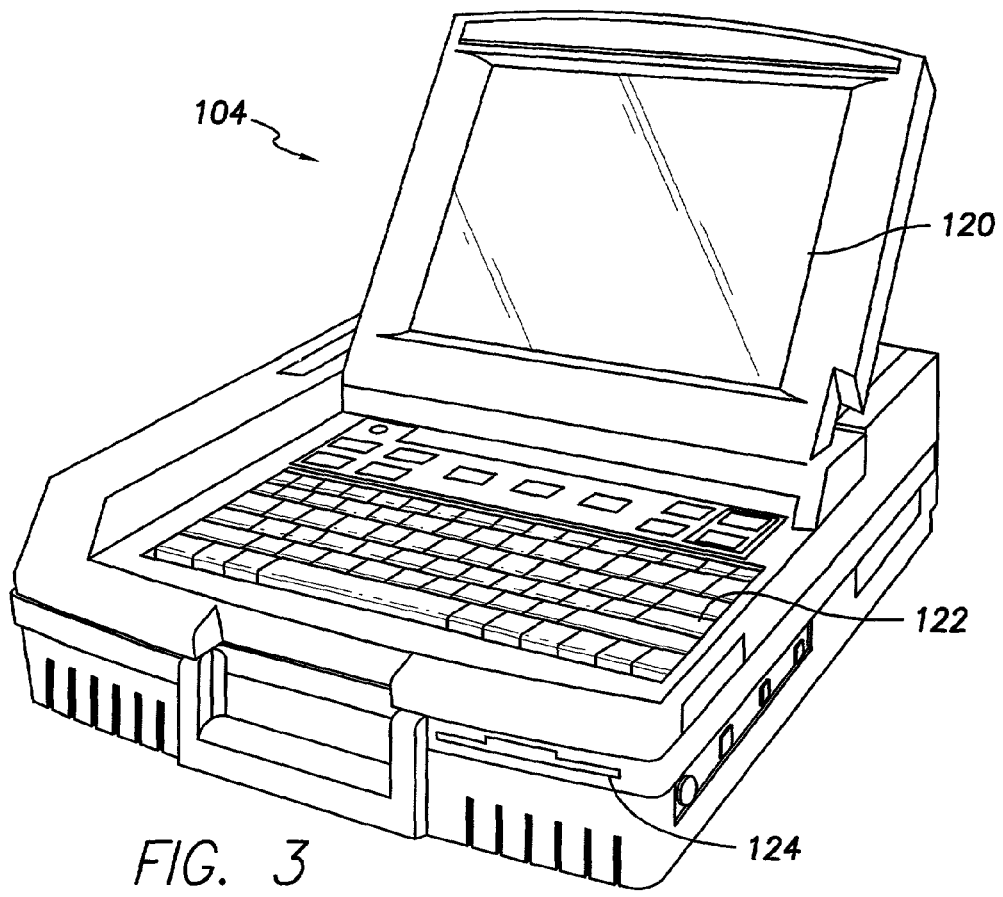
FIG. 3 is a perspective view of an implantable cardiac device programmer with wireless communication with a surface ECG unit.
Figure 4:
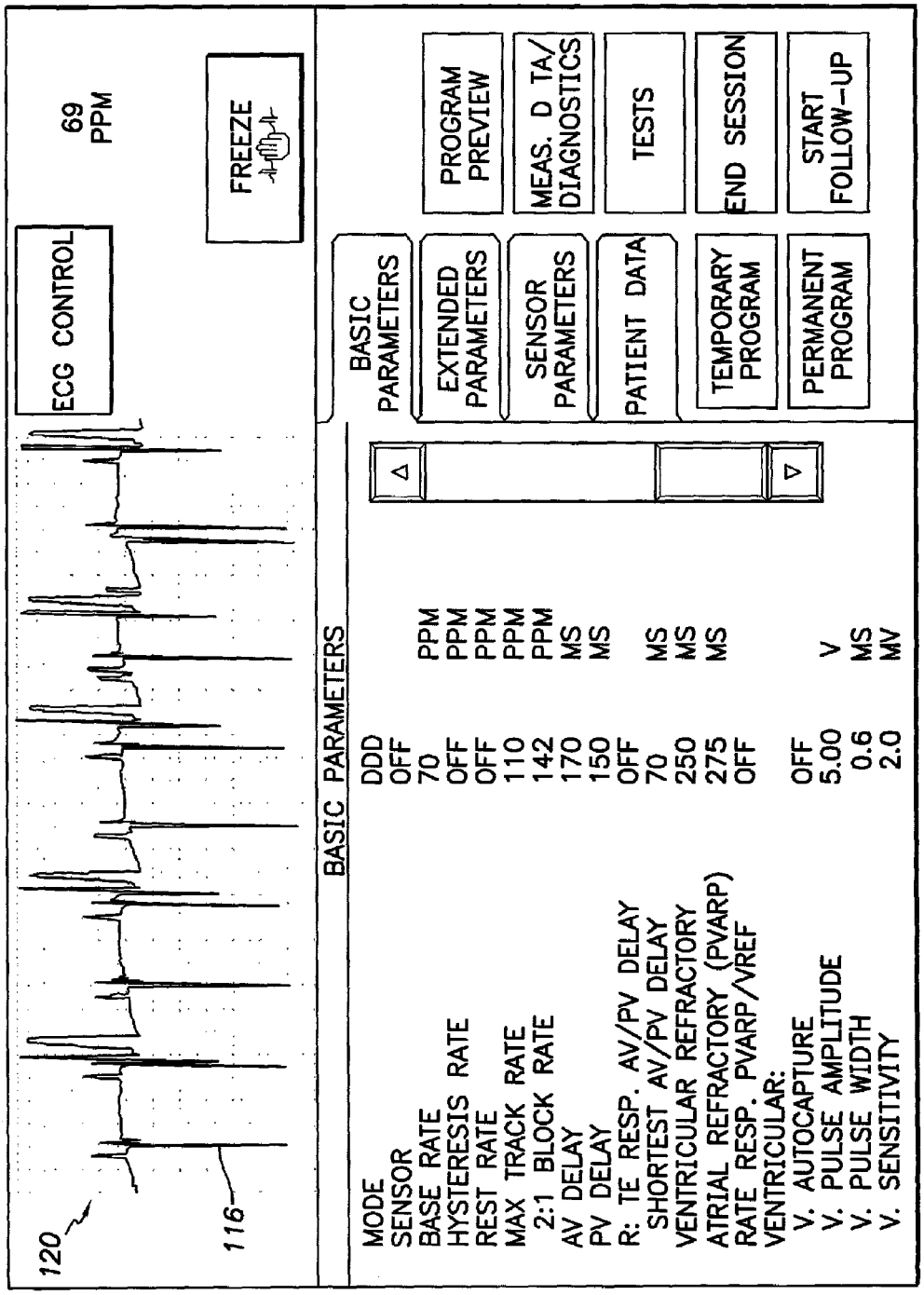
FIG. 4 is a screen capture of one embodiment of the system of FIG. 1.

FIG. 3 illustrates one embodiment of the programmer 104. The programmer 104 comprises a display screen 120, at least one input device 122, and a removable storage device 124. The display screen 120 provides information relating to the operation of the ECG monitor 102 and the implantable cardiac device in a known manner. An example of one embodiment of the information provided by the display screen 120 is illustrated in FIG. 4 and will be described in greater detail below. The input device 122 is adapted to enable a user to input commands to the programmer 104 in a known manner. The input device 122 in the embodiment illustrated in FIG. 3 comprises a keyboard of a type well known in the art, however, the input device 122 can also comprise touch screens, touch mouse pads, speech recognition systems, or other input mechanisms in alternative embodiments of the invention.

The removable storage device 124 enables a user to store information relating to a patient's condition and treatment in a removable, non-volatile manner. In one embodiment, as illustrated in FIG. 3, the removable storage device 124 comprises a standard 3½" disk drive and removable disks of types well known in the art. In other embodiments, the removable storage device 124 comprises a read/write CD-ROM drive and rewritable CDs and/or flash memory systems also of types well known in the art. Additional features and functions of the programmer 104 will be described in greater detail below with reference to FIG. 4 and FIG. 7.

FIG. 4 illustrates a screen capture of one embodiment of the display screen 120 of the programmer 104. The display screen 120 presents a visual representation of the underlying cardiac activity as sensed by the system 100 as an ECG waveform 116. In this embodiment, the ECG waveform 116 can be displayed as a real-time, dynamic scrolling display or a time slice of the ECG waveform 116 can be frozen to enable a clinician to investigate in greater detail a representative sample of the ECG waveform 116. As shown in FIG. 4, in this embodiment, the display 120 of the programmer also provides a plurality of user selectable controls for the programmer 104.

As illustrated in FIG. 4, the programmer 104 is set to a basic parameters option. In this option, certain basic sensed parameters, such as the base rate, the AV delay, PV delay, and others, are displayed. The programmer 104 of this embodiment also provides the ability to alter/set operational parameters of the implantable device, such as ventricular autocapture, which, in the embodiment illustrated, is selected "Off". It can be further seen that the programmer 104 provides additional extended parameter display, more detailed patient data, and sensor parameter information and control. This aspect is useful to a clinician in remotely setting parameters of the sensor portions of the implantable device, such as threshold levels in a non-invasive manner via, the first telemetric link 105. The programmer 104 also includes the capability, in certain embodiments, to select the electrodes 100, 111 that pass their respective signals, via the transceiver 112, to the programmer 104 in a manner that will be described in greater detail below.

It will be appreciated that the specific functionalities and information provided by the programmer 104 can vary among different applications. It is therefore preferred that the programmer 104 be programmable and user-customizable. For example, as illustrated in FIG. 4, the programmer 104 of this embodiment has provision for both temporary and permanent programming as well as automated tests and diagnostic functions. The programmable aspects of the programmer 104 can include provisions for interfacing with different versions of implantable medical devices, operating in different radio frequencies, and storing data specific to different patients.

Figure 5:
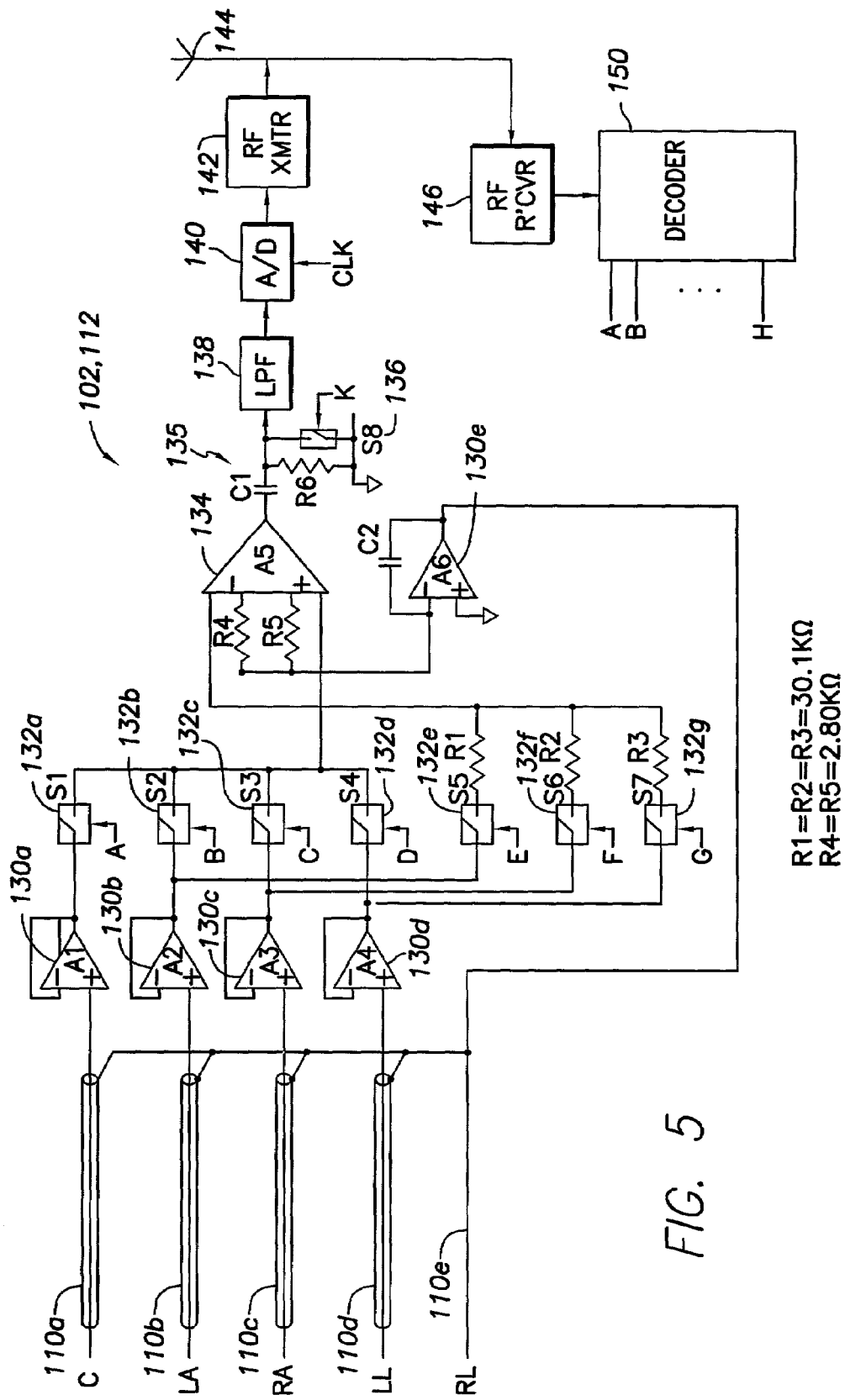
FIG. 5 is a circuit diagram of one embodiment of the system of FIG. 1.

FIG. 5 illustrates in greater detail a circuit block diagram of the surface ECG monitor 102. The surface ECG monitor 102 monitors and selectively transmits a surface ECG signal as sensed by a plurality of electrodes 110, 111 in a plurality of lead configurations. In this embodiment, the surface ECG monitor 102 comprises the 5 electrodes 110a–110e with electrode 110a designating the C (center) electrode, 110b designating the LA (left arm) electrode, 110c designating the RA (right arm) electrode, 110d the LL (left leg) electrode, and 110e the RL (right leg) electrode. As previously described, the electrodes 110a–110e sense and conduct electrical signals from the patient's skin surface indicative of underlying cardiac activity. Proper placement and attachment of the electrodes 110a–110e on the patient for the C, LA, RA, LL, and RL positions is well understood by one of ordinary skill in the art.

The surface ECG monitor 102 also comprises, in this embodiment, 4 amplifiers 130a–130d. Each of the electrodes 110a–10d is connected to the non-inverting input of each of the amplifiers 130a–130d respectively. The inverting input of each of the amplifiers 130a–130d is connected to the outputs of each of the amplifiers 130a–130d respectively. The output of each of the amplifiers 130a–130d is also connected to one pole of a switch 132a–132d respectively. The switches 132a–132d facilitate selection by a clinician of which of the electrodes 110a–110d pass their signal through the surface ECG monitor 102 and thus on to the programmer 104. The opposite poles of the switches 132a–132d are commonly connected to the non-inverting input of an amplifier 134.

The surface ECG monitor 102 also comprises switches 132e–132g. One pole of each of the switches 132e–132g is connected to the output of the amplifiers 130b–130d respectively. The opposite poles of each of the switches 132e–132g are connected in parallel via, in this embodiment, a 30.1 kΩ resistor, in common to the inverting input of the amplifier 134.

The output of the amplifier 134 is connected to a high pass filter 135. The high pass filter 135 filters out DC offsets due to electrode-skin interfaces and the amplifier A5 134. In one embodiment, the high pass filter 135 comprises a capacitor, C1 and resistor, R6 as shown in FIG. 5. In one particular embodiment, a value of C1 of 0.33 µF and a value of R6 of 10 MΩ gives a corner frequency of $f=1/2\pi RC=0.05$ Hz.

In this embodiment, a switch, S8 136 is also provided. The switch, S8 136, in this embodiment, can be momentarily closed by the programmer 104 to speed up the baseline coming to zero. The momentary closure of switch S8 136 will quickly charge the capacitor C1 of the high pass filter 135, thus removing any DC offset. The output of the amplifier 134 is connected, via the high pass filter 135 and the switch 136, to the input of a low pass filter (LPF) 138.

The output of the LPF 138 is connected to the input of an analog-to-digital (A/D) converter 140. The A/D 140 converts the analog multiplexed signals received from the electrodes 110a–110e, as selected by the switches 132a–132g and digitizes these signals in a well understood manner. The digitized surface ECG signal is then sent from the output of the A/D 140 to a radio-frequency (RF) transmitter 142. The RF transmitter 142 transmits the digitized surface ECG signals via an antenna 144 to the programmer 104 in a manner well understood by one of ordinary skill in the art.

In this embodiment, the surface ECG monitor 102 also comprises a radio frequency (RF) receiver 146 in communication with the antenna 144. The RF receiver 146 receives radio-frequency transmissions from the programmer 104 via the antenna 144 and passes these signals to a decoder 150. In this embodiment, the decoder 150 is an 8 bit digital-to-analog (D/A) converter. In this embodiment, the 8(a–h) digital outputs of the decoder 150 are connected to the switches 132a–132g and 136, respectively, such that setting/clearing the various outputs of the decoder 150 can close/open each of the switches 132a–132g and 136 individually depending on the signal received by the RF receiver 146. As previously mentioned, according to this aspect of the invention, each of the switches 132a–132g can be remotely, telegraphically controlled, such as by the programmer 104, to vary which of the electrodes 110a–110e have their respective signals processed by the surface ECG monitor 102 and thus transmitted by the RF transmitter 142.

Thus, according to this aspect, a clinician or other user can alter the lead configuration provided by the 5 electrodes 110a–110e directly with the programmer 104 without physical contact with the patient following initial attachment of the electrodes 110a–110e via the second telemetric link 106. Thus, the clinician can readily select among the available lead configurations without physically detaching or disconnecting the electrodes 110a–110e attached to the patient. It will be appreciated that, in alternative embodiments, signals from all of the electrodes 110, 111 are transmitted by the surface ECG monitor 102 and the programmer 104 selects locally from among the electrode 110, 111 signals to generate the ECG waveform 116 for the display screen 120.

The table of FIG. 6 shows the lead configurations of one embodiment with the corresponding position of the switches 132a–132g. For one example, the aVF lead configuration is selected when switches 132d–132f are closed (on) so as to conduct the signal from the electrode 110d, i.e. the LL electrode, to the non-inverting input of the amplifier 134 as well as the combined signals from the electrodes 110b and 110c, i.e. the LA and RA electrodes, to the inverting input of the amplifier 134. The other switches 132a, 132b, 132c, and 132g are open and their respective electrode 110 signals are opened from the inputs of the amplifier 134. The other lead configurations I, II, III, aVR, aVL, V, and null provided by other switch 132a–132g positions, as presented in FIG. 6, as well as selection of appropriate lead configurations for a given clinical circumstance will be well understood by one of ordinary skill in the art following the above example.

Lead I is defined as the RA signal as the −input and the LA signal as the +input. Lead II is defined as the RA signal as the −input and the LL signal as the +input. Lead III is defined as the LA signal as the −input and the LL signal as the +input. The aVR lead is defined as the (LA+LL)/2 signal as the −input and the RA signal as the +input. The aVL lead is defined as the (RA+LL)/2 signal as the −input and the LA signal as the +input. The aVF lead is defined as the (RA+LA)/2 signal as the −input and the LL signal as the +input. The V lead is defined as the (RA+LA+LL)/3 signal as the −input and the C signal as the +input.

Figure 7:
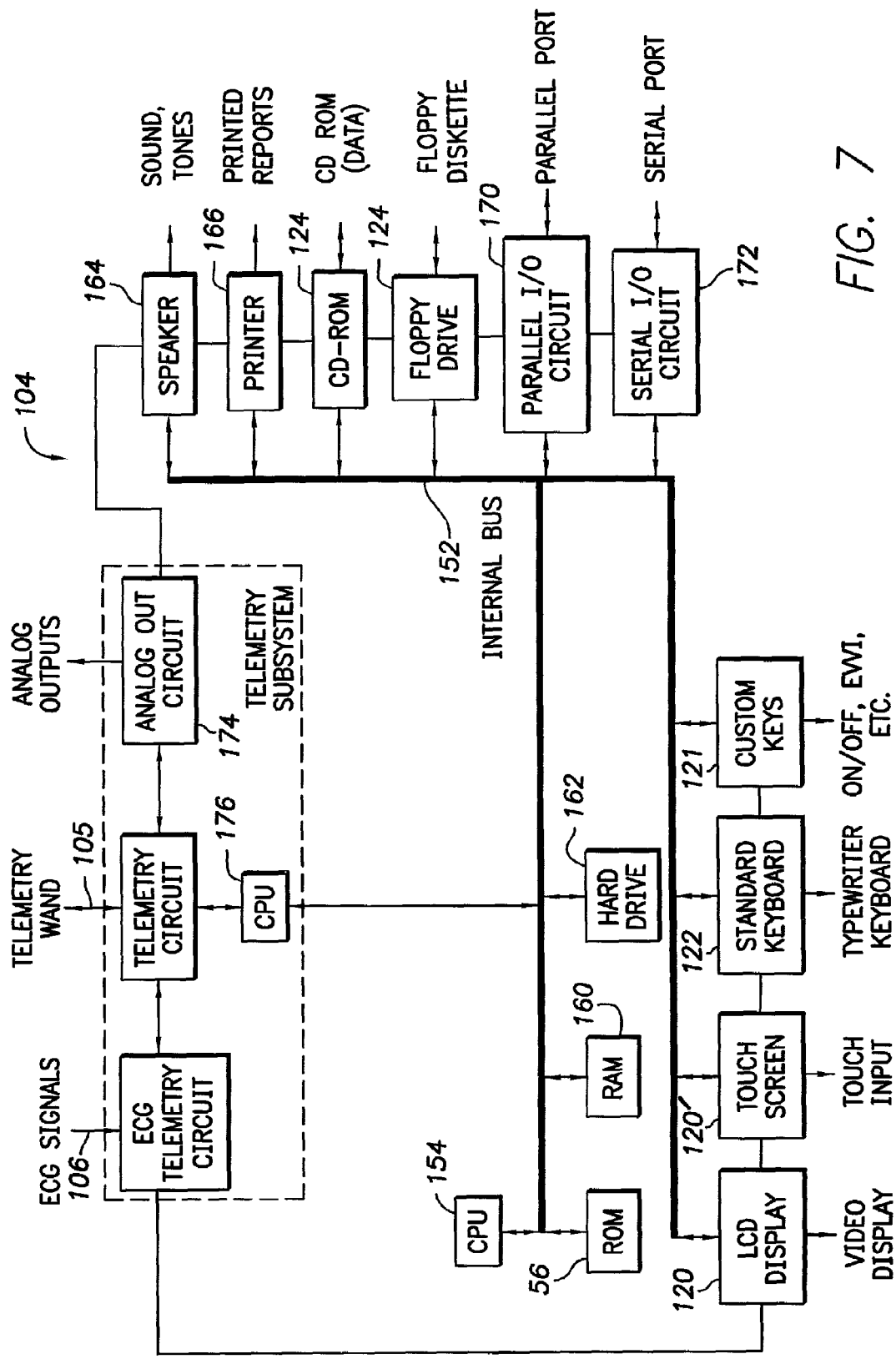
FIG. 7 is a functional block diagram of one embodiment of the programmer.

FIG. 7 is a functional block diagram of one embodiment of the programmer 104 in greater detail. As previously mentioned, the programmer 104 receives surface ECG signals from the ECG monitor 102 via the second telemetric link 106 and displays them as the ECG waveform 116 on the display 120. The programmer 104 also receives user commands via the input device(s) 122 and induces the ECG monitor 102 and/or the implantable device to perform specified actions via the first telemetric link 105.

In this embodiment, the programmer 104 comprises an internal bus 152 and a central processing unit (CPU) 154. The CPU 154 interfaces with other components of the programmer 104 via the internal bus 152 and directs their operation in a manner well understood in the art. The programmer 104 also comprises read-only-memory (ROM) 156, random-access-memory (RAM) 160, and a hard drive 162. The ROM 156, RAM 160, and hard drive 162 are in communication with the internal bus 152 and provide the programmer 104 short term memory and long term, non-volatile storage capability in a well known manner. As previously mentioned, the programmer 104 comprises a storage device which can comprise the floppy drive and diskette as illustrated in FIG. 3 and the CD-ROM and drive as illustrated in FIG. 7 as well as other non-volatile storage systems, such as flash memory.

The programmer 104 also optionally includes a speaker 164, printer 166, parallel port 170, and/or serial port 172. The speaker 164 is adapted to provide auditory alerts and indicators and the printer 166 is adapted to provide a written record of data, such as a portion of the ECG waveform 116, or a summary of the information provided by the display 120, such as patient data. The parallel port 170 and the serial port 172 are adapted to interface with other electronic devices in a parallel or serial manner, respectively. The exact manner and format of the parallel or serial communication performed by the parallel 170 and serial 172 ports, respectively, may vary in different applications.

As previously mentioned, the display 120 presents a user with visual information. The display 120 can also optionally comprise a touch-screen 120' to enable the display 120 to operate at least partially as an input device 122. The programmer 104 also preferably includes the user-customizable functionality of custom keys 121. The custom keys 121 enable a user to program frequently used or personal preference functions of the programmer 104. In certain embodiments, the custom keys 121 are embodied in the touch screen 120' of the display 120. In other embodiments, the custom keys 121 are user definable keys or key combinations of the input device 122.

The programmer 104 in certain embodiments also transceives analog signals. In certain embodiments, the analog communication occurs via an analog output circuit 174 via hardwired analog outputs. In other embodiments, the first telemetric link 105 is adapted to transceive analog format signals in a well known manner.

The programmer 104 also comprises a telemetry CPU 176. The telemetry CPU 176 is in communication with the CPU 154 via the internal bus 152. The telemetry CPU 176 directs and monitors the operation of the telemetric links 105, 106.

Although FIG. 7 illustrates two separate telemetry circuits in the programmer 104 under control of the telemetry CPU 176 providing the first 105 and second 106 telemetric links with the implantable device and the surface ECG monitor 102, the first and second telemetric links 105, 106 can also comprise different RF channels, different communication formats such as amplitude modulation (AM), frequency modulation (FM), frequency shift keying (FSK), quadrature phase shift keying (QPSK), time multiplexing or time slotted communications, such as time division multiple access (TDMA), or packet addressing in a variety of implementations well known in the art in alternative embodiments of the system 100.

Although the preferred embodiments of the present invention have shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. A therapeutic stimulation and monitoring system for a patient's heart comprising:

an implantable cardiac stimulation and physiological parameter monitoring device;

a programmer adapted to transceive wireless signals with the implantable device over a first channel so as to induce the implantable device to alter the therapeutic stimulation and monitored physiological parameters provided and to transmit signals indicative of the monitored physiological parameters to the programmer;

means for monitoring surface signals of the patient indicative of cardiac activity including means for transceiving wireless signals with the programmer over a second channel so as to provide the programmer with signals indicative of the surface signals of the patient and to receive signals inducing the monitoring means to alter the configuration of the surface signal provided to the programmer, wherein the first and a second channels comprise first and second time division channels.

2. The therapeutic stimulation and monitoring system of claim 1, wherein the programming means further comprises display means for displaying signals indicative of the surface signals of the patient.

3. The therapeutic stimulation and monitoring system of claim 2, wherein the surface signals comprise a surface electrocardiogram.

4. The therapeutic stimulation and monitoring system of claim 3, wherein the surface signal comprises at least one of a Lead I, Lead II, Lead III, $aV_R$ Lead, an $aV_L$ Lead, an $aV_F$, or a V Lead.

5. The therapeutic stimulation and monitoring system of claim 2, wherein the monitoring means provides the programmer with signals selected from among a plurality of the surface signals.

6. The therapeutic stimulation and monitoring system of claim 5, wherein the monitoring means selects among the plurality of surface signals in response to wireless signals from the programmer.

7. A therapeutic stimulation and monitoring system for a patient's heart comprising:

an implantable cardiac stimulation and physiological parameter monitoring device;

a programmer adapted to transceive wireless signals with the implantable device so as to induce the implantable device to alter the therapeutic stimulation and monitored physiological parameters provided and to transmit signals indicative of the monitored physiological parameters to the programmer; and means for monitoring surface signals of the patient indicative of cardiac activity including means for transceiving wireless signals with the programmer so as to provide the programmer with signals indicative of the surface signals of the patient and to receive signals inducing the monitoring means to alter the configuration of the surface signal provided to the programmer, wherein the means for monitoring surface signals includes a plurality of switches that are manually actuated to select among the plurality of surface signals.

8. The therapeutic stimulation and monitoring system of claim 1, wherein at least one of the first and second channels comprise an RF channel that operates in the 900 MHz band.

* * * * *